US00PP18133P2

(12) United States Plant Patent
Brooks

(10) Patent No.: US PP18,133 P2
(45) Date of Patent: Oct. 23, 2007

(54) ***ECHINACEA* PLANT NAMED 'ELTON KNIGHT'**

(50) Latin Name: *Echinacea purpurea*
Varietal Denomination: Elton Knight

(76) Inventor: Anthony Brooks, Holly Tree Cottage, Elton, Ludlow, Shropshire (GB), SY8 2HQ ( * ) Notice: Subject to any disclaimer, the term of this patent is extended or adjusted under 35 U.S.C. 154(b) by 46 days.

(21) Appl. No.: 11/412,358

(22) Filed: Apr. 26, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para

(57) ABSTRACT

A new and distinct cultivar of *Echinacea* plant named 'Elton Knight' characterized by a compact habit, multi-branched stems, horizontal ray florets, and a bright magenta flower color.

3 Drawing Sheets

Genus: *Echinacea.* Species: *purpurea.*
Denomination: 'Elton Knight'.

BACKGROUND OF THE INVENTION

The present Invention relates to a new and distinct cultivar of coneflower that may be grown for use as an ornamental plant in containers and in the garden or landscape. The new cultivar is known botanically as *Echinacea purpurea* and will be referred to hereinafter by the cultivar name 'Elton Knight'.

The inventor is the designated holder, at his garden in Shropshire, England, of the United Kingdom National Collection of *Echinaceas* which includes the majority of the commercially available seed-raised strains and clonal cultivars of the genus. In 1992, the inventor selected two varieties from the Collection with the intention of breeding a valuable new cultivar. First, the inventor selected as the seed parent the variety *Echinacea purpurea* 'Rosenelf' (unpatented) which the inventor has admired for its short compact habit, clean flower color with less inclination to fade and a large central orange cone. Second, the inventor selected as the pollen parent the variety *Echinacea purpurea* 'The King' (unpatented) which is notable for the exceptional branching of its stems so that a whole plant carries a large number of flowers. The inventor hoped to be able to combine the characteristics of the parents into a new cultivar which is short and compact and well branched, leading to a dense display of flowers.

During 1994, the inventor was able to evaluate the plants which he had raised and planted out as seedlings from the seed collected from the cross described above. One plant, which is the subject of the present invention 'Elton Knight', was identified and selected as possessing the most attractive combination of the desired characteristics. Since that time, the inventor has maintained 'Elton Knight' in his garden and has asexually reproduced 'Elton Knight' by division, and has determined that 'Elton Knight' is stable and reproduces true to type in successive generations of asexual reproduction.

The inventor has observed 'Elton Knight' over time and has determined that it is different from both the parent cultivars and from other cultivars of *Echinacea* known to the inventor, in the following respects:

The seed parent *Echinacea purpurea* 'Rosenelf' is a short compact variety with flowers borne on single unbranched stems resulting in a very few flowers per plant. The pollen parent, *Echinacea purpurea* 'The King' has many branched stems giving many more flowers on a single plant but is a tall plant which requires staking. In comparison with its parents, 'Elton Knight' is both short and compact (approximately one half of the height of 'The King') with multi-branched flower stems resulting in a dense display of flowers. 'Elton Knight' does not require staking.

A widely grown strain of *Echinacea* is distributed as *Echinacea purpurea,* 'Bressingham hybrids'. The inventor has observed that 'Elton Knight' is different from 'Bressingham hybrids'. 'Elton Knight' achieves a height of approximately 60 cm and requires no staking, whereas 'Bressingham hybrids' are taller at 100 cm and require staking. 'Elton Knight' has horizontal petals which do not droop as the flower matures and ages, whereas 'Bressingham hybrids' exhibit the typical drooping petals of *Echinacea.* The stems of 'Elton Knight' are attractive dark purple in color, whereas the stems of 'Bressingham hybrids' are green. 'Elton Knight' has multi-branched stems with many flowers on each plant compared to 'Bressingham hybrids' which carries fewer flowers on single stems.

In conclusion, the inventor considers that 'Elton Knight' is a very robust plant whose vibrant magenta flowers are less inclined to fade than the flowers of other *Echinaceas* known to the inventor. The dark green foliage of 'Elton Knight' sets off the flowers well and a mature plant of 'Elton Knight' exhibits an interesting mix of new and faded flowers while maintaining its shape. Finally, 'Elton Knight' makes a very good cut flower with long-lasting qualities.

Commencing in 2001 and ending in 2003, The Royal Horticultural Society of England carried out evaluations of twenty one cultivars of *Echinacea* in their invited trial for the purpose of determining if any of the entries should be accorded an Award of Garden Merit. The trials took place at a secure non-public location within the Society's Garden in Wisley, England. The inventor entered 'Elton Knight' into these trials and provided the test plants and is satisfied that the test plants were not propagated or distributed to any third party. The plants were evaluated by the Floral Trials subcommittee on eight separate occasions, and 'Elton Knight' was unanimously proposed for the Award. Although The Royal Horticultural Society published the results of the Trial during 2004, the first public sale of 'Elton Knight' took place on May 4, 2005.

SUMMARY OF THE INVENTION

The cultivar 'Elton Knight' has not been observed under all possible environmental conditions. The phenotype may be different somewhat with variations in environment such as temperature and light intensity without, however, any variance in genotype. The following traits have been repeatedly observed and are determined to be the unique characteristics of 'Elton Knight'.

1. *Echinacea* 'Elton Knight' has a short, compact plant habit, typically 60 cm high after one growing season.
2. *Echinacea* 'Elton Knight' is an herbaceous perennial.
3. *Echinacea* 'Elton Knight' has vibrant magenta flowers.
4. *Echinacea* 'Elton Knight' has dark purple stems.
5. *Echinacea* 'Elton Knight' displays horizontal petals.
6. *Echinacea* 'Elton Knight' has an orange cone composed of many disc florets.

BRIEF DESCRIPTION OF THE DRAWINGS

The accompanying color drawings illustrate the overall appearance of the new *Echinacea* cultivar 'Elton Knight' showing the colors as true as it is reasonably possible to obtain in colored reproductions of this type. Colors in the photographs may differ from the color values cited in the detailed botanical description, which accurately describe the actual colors of the new variety 'Elton Knight'.

Figure 1:
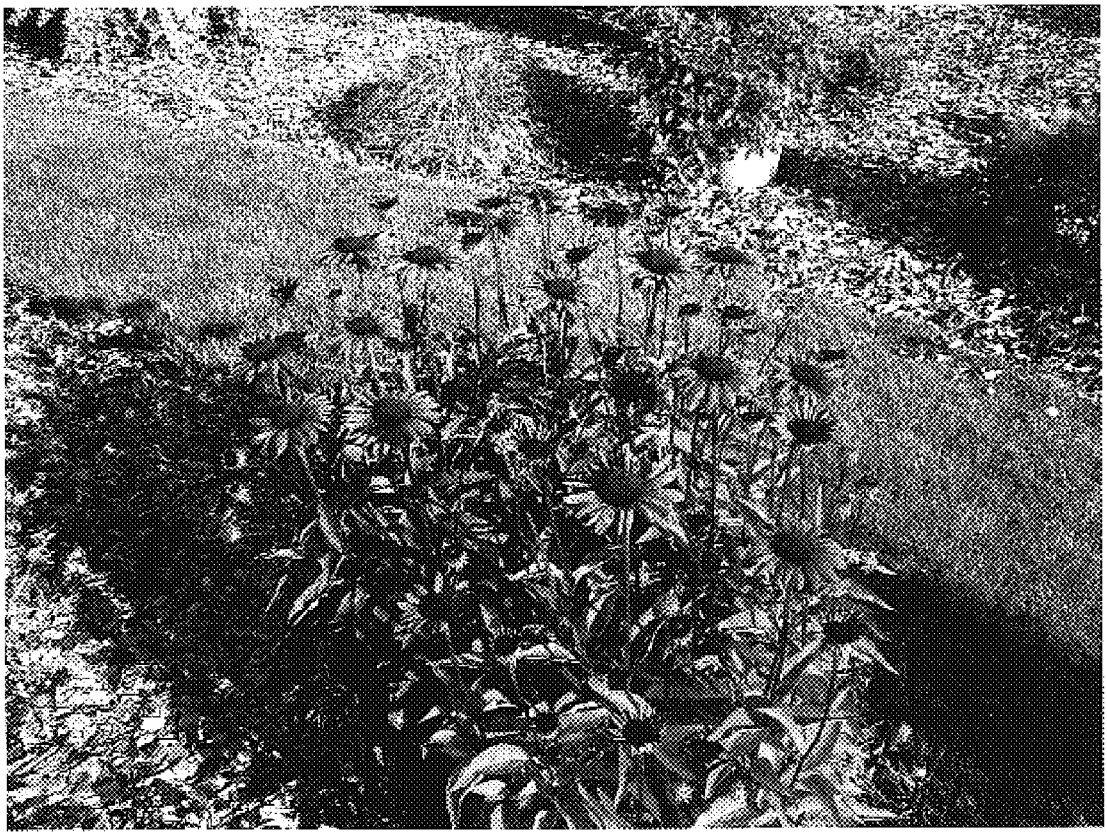
FIG. 1 illustrates an entire plant of 'Elton Knight' in bloom, from a side perspective. This plant is approximately 18 months old and is planted outdoors in Cambridgeshire, England.
Figure 2:
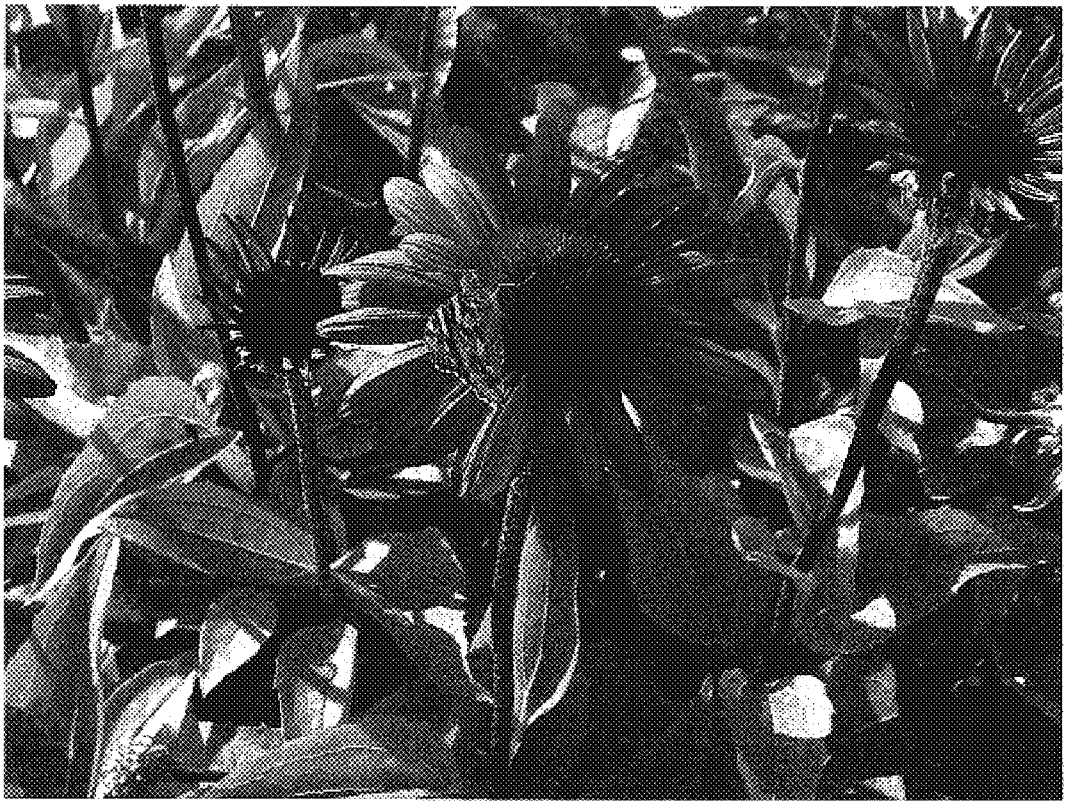
FIG. 2 illustrates a close-up view of the inflorescence of the 18 month old plant in FIG. 1 showing both ray florets and the disc florets which constitute the typical spiny cone of *Echinacea*.
Figure 3:
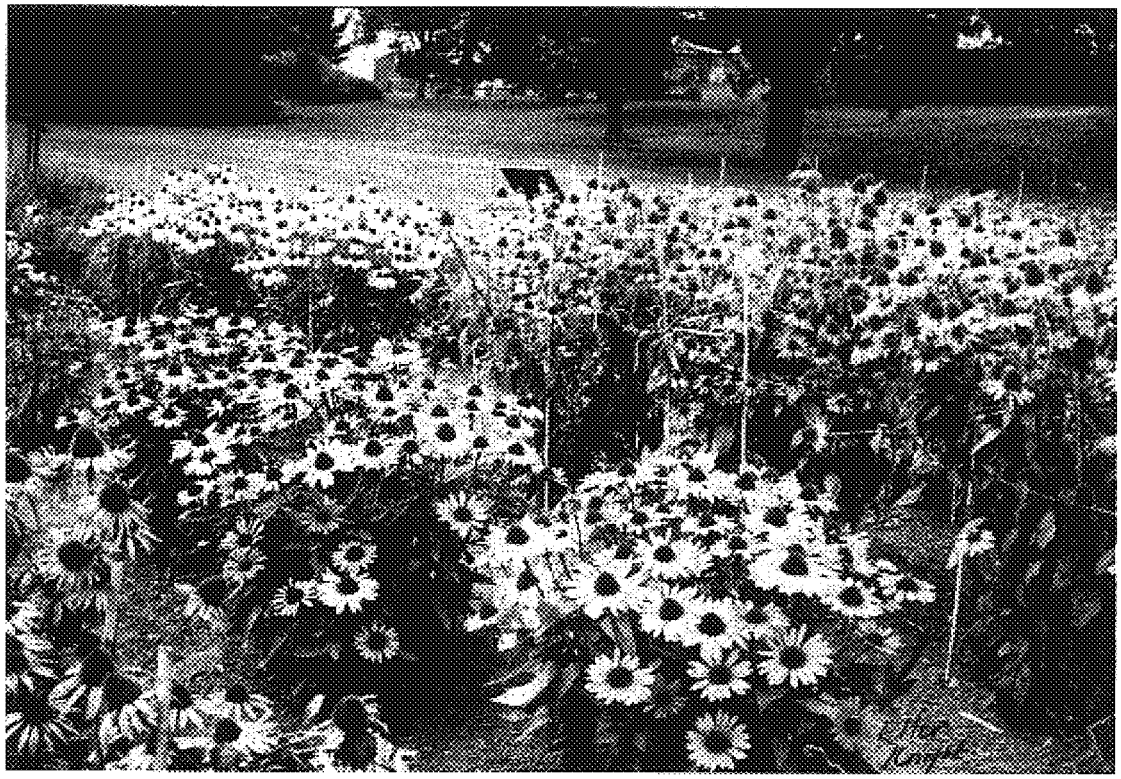
FIG. 3 illustrates a planting of 'Elton Knight' in a private trial bed at The Royal Horticultural Society in Wisely, United Kingdom. The plants in the middle section of plants are 30 months old and illustrate the tight low habit and horizontal petals of 'Elton Knight' especially when compared to the cultivars next to them. *Echinacea* 'The King' is the plant in the lower left section and the 'Bressingham hybrids' are in the upper right section.

The drawings are made using conventional photographic techniques and although flower and foliage colors in the photographs may differ from the actual colors due to light reflectance, they are as accurate as conventional photography can portray.

BOTANICAL DESCRIPTION OF THE PLANT

The following observations and measurements describe plants of 'Elton Knight' grown outdoors in Cambridgeshire, England.

The observed plants were approximately two years old from a single division.

Color observations were made by reference to the 2001 edition of The Royal Horticultural Society Colour Chart, except where general terms of ordinary dictionary significance are used.

Botanical classification:
- *Genus.*—*Echinacea.*
- *Species.*—*purpurea.*
- *Cultivar denomination.*—'Elton Knight'.
- *Parentage.*—Pollen parent: *Echinacea purpurea* 'The King'. Seed Parent: *Echinacea purpurea* 'Rosenelf'.

Propagation:
- *Method.*—Division.
- *Time to produce a rooted plant.*—Division (with roots attached) 10 days to re-establish.
- *Root description.*—Deep, fine, fibrous, well-branched.

Overall plant description:
- *Appearance.*—Herbaceous perennial with upright habit and short stature.
- *Vigor.*—Vigorous.
- *Dimensions.*—60 cm in height, 45 cm in width.
- *Growing conditions.*—Soil types: Moderately fertile, well-drained border soil. Light: Partial shade to full sun. Hardiness: USDA Zone 3. Pest and Disease Resistance and Susceptibility: None of note in comparison with the genus *Echinacea* which can be susceptible to chewing insects and to pathogens including *fusarium, sclerotinia, phytophthera, verticillium.*

Foliage:
- *Branching habit.*—Produces 1 to 4 laterals per stem.
- *Branch angle at emergence.*—45°.
- *Stem.*—Color: Between 144B and 146C with elongated spots of N187A. Cross-section: Round with central pithy cavity. Length of main stem: 58 cm to 61 cm. Pubescence: Moderately to densely clothed with bristly hairs. Pubescence color: Greenish white, too fine to color match. Lenticels: Absent. Internode length: 37 mm to 82 mm.
- *Leaves.*—Basal Leaves Dimensions: 94 mm to 133 mm in length, 67 mm to 87 mm in width. Shape: Cordate to ovate. Arrangement: Rosette. Margins: Serrate. Division: Absent. Apex shape: Acute. Base shape: Cordate, sometimes rounded. Color of adaxial surface: Lamina between 137A and 139A, veins 145D. Color of abaxial surface: Lamina between 147B and 147C, veins between 145 C and 145D. Pubescence (adaxial and abaxial): Moderate with short, bristly hairs. Venation pattern: Palmate. Fragrance: Absent. Attachment: Petiolate. Petiole dimensions: 85 mm to 160 mm in length, 2 mm to 3 mm in diameter. Petiole color: 186A at the extreme base merging to between 143C and 143D near the lamina. Petiole pubescence: Sparsely bristly-hairy in the upper half. Stipules: Absent. Stem Leaves Dimensions: 113 mm to 132 mm in length, 53 mm to 73 mm in width. Shape: Ovate. Arrangement: Alternate. Margins: Serrate. Division: Absent. Apex shape: Acute to attenuate. Base shape: Rounded-attenuate. Color of adaxial surface: Lamina between 137A and 139A, veins 145D. Color of abaxial surface: Lamina between 147B and 147C, veins between 145 C and 145D. Pubescence (adaxial and abaxial): Moderate with short, bristly hairs. Venation pattern: Pinnate. Fragrance: Absent. Attachment: Petiolate. Petiole dimensions: 28 mm to 47 mm in length, 3 mm to 5 mm in diameter. Petiole color: Between 144C and 144D, lightly tinged along the middle with 186A.

Petiole pubescence: Bristly-hairy along the margins. Stipules: Absent.

Inflorescence:

*Flowering period.*—June through October.

*Number of individual flowers (flower heads).*—1.

*Lastingness of flowers on the plant.*—2 to 3 weeks as flowers fade.

*Lastingness of flowers off the plant.*—2 weeks.

*Fragrance.*—None observed.

*Peduncle.*—Dimensions: 133 mm to 156mm in length, 4 mm to 6 mm in diameter becoming broader immediately below the capitulum. Color: 146C heavily flecked with N187B. Pubescence: Moderately to densely pubescent, hairs bristly.

*Flower bud dimensions.*—2 cm in length and 3.5 cm in width.

*Flower bud shape.*—Truncate.

*Flower bud color.*—Between 137A and 139A.

*Flower head, persistent or self-cleaning.*—Persistent.

*Involucre.*—Number of bracts: Numerous, in 4 series. Outer bract dimensions: 15 mm in length, 3 mm in width. Outer bract shape: Narrow triangular. Outer bract tip shape: Sharply acute. Outer bract margin: With numerous very short bristles. Outer bract attitude: Strongly reflexed. Outer bract pubescence: Absent on both surfaces.

*Flower head.*—Aspect: Upright. Overall height: 35 mm at anthesis of first disc florets, becoming greater later. Overall diameter: 110 mm. Fragrance: Weak. Number of ray florets: 21 to 24. Ray floret: Attitude: Horizontal. Calyx: Number of lobes: 5. Shape of lobes: Narrow triangular. Shape of tips of lobes: Acuminate. Length of lobes: 3 mm. Width of tips of lobes: 1 mm. Color of lobes: 144C. Corolla: Overall length: 52 mm. Shape: Elliptic-obovate. Length of tube: Tube absent: ligule extends to the corolla base. Width: 10 mm. Shape: Elliptic-obovate. Shape of tip: Short bifid with two acute points. Color of adaxial surface: 64A. Color of abaxial surface: 186B tinged with 139D toward the base and tip. Texture: Smooth. Longitudinal axis: Weakly recurved. Cross-section at midpoint: Flat, becoming convex with age. Stamens: Absent. Stigma: Absent. Ovary dimensions: 2 mm length and 1 mm width.

*Disc.*—Profile: Slightly domed when outermost disc florets are at anthesis, becoming more strongly domed later. Diameter: 35 mm. Color before and at anthesis: Between 177A and 200A. Disc florets: Dimensions: 11 mm in length and 1.5 mm in diameter. Calyx: Thin and transparent, consisting of 5 triangular lobes 1 mm long and less than 1 mm wide. Corolla: Dimension of tube: 5 mm in length and 1.5 mm in diameter. Color: 144D. Number of lobes: 5. Shape of lobes: Triangular with acute tips. Dimensions of lobes: 1 mm in length and less than 1 mm in width. Color of lobes: 138B.

*Reproductive organs.*—Stamens: Fused to form a tube round the stigma, anthers and filaments indistinguishable, projecting 1.5 mm beyond the corolla, color 138B. Pollen amount: Copious. Pollen color: 14A. Number of carpels: 1 Stigma length: Projecting 2 mm beyond the stamen tube. Stigma shape: Bilobed, the thread-like lobes recurving strongly. Stigma color: 187A. Ovary dimensions: 2 mm in length and less than 1 mm in width. Ovary color: 155A.

*Seed.*—None observed.

It is claimed:

1. A new and distinct variety of *Echinacea* plant named 'Elton Knight' as described and illustrated herein.

* * * * *